(12) United States Patent
Wendlandt et al.

(10) Patent No.: US 10,271,802 B2
(45) Date of Patent: Apr. 30, 2019

(54) DIGITAL X-RAY IMAGING APPARATUS AND METHOD

(71) Applicant: Carestream Health, Inc., Rochester, NY (US)

(72) Inventors: William C. Wendlandt, Rush, NY (US); James H. Ogle, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 417 days.

(21) Appl. No.: 14/822,924

(22) Filed: Aug. 11, 2015

(65) Prior Publication Data

US 2016/0045174 A1 Feb. 18, 2016

Related U.S. Application Data

(60) Provisional application No. 62/036,287, filed on Aug. 12, 2014.

(51) Int. Cl.
*A61B 6/00* (2006.01)
*A61B 6/10* (2006.01)

(52) U.S. Cl.
CPC .......... *A61B 6/105* (2013.01); *A61B 6/4405* (2013.01); *A61B 6/467* (2013.01)

(58) Field of Classification Search
CPC ...................................................... H05G 1/02
See application file for complete search history.

(56) References Cited

U.S. PATENT DOCUMENTS

| | | | | |
|---|---|---|---|---|
| 4,326,131 | A * | 4/1982 | Waerve | H05G 1/02 378/193 |
| 5,067,145 | A * | 11/1991 | Siczek | A61B 6/4405 378/198 |
| 5,081,662 | A * | 1/1992 | Warden | A61B 6/4405 378/193 |
| 5,283,823 | A * | 2/1994 | Morris | A61B 6/4405 378/193 |
| 5,499,284 | A * | 3/1996 | Pellegrino | A61B 6/4405 378/197 |
| 6,409,382 | B1 * | 6/2002 | Akutsu | A61B 6/4405 378/114 |
| 7,165,885 | B2 * | 1/2007 | Lumma | A61B 6/105 378/167 |
| 7,438,470 | B2 * | 10/2008 | Koren | A61B 6/00 378/198 |
| 7,802,642 | B2 * | 9/2010 | Jensen | A61B 6/4441 180/6.48 |
| 8,376,612 | B2 * | 2/2013 | Takae | A61B 6/4283 378/198 |
| 8,419,276 | B2 * | 4/2013 | Oda | A61B 6/4283 378/198 |
| 8,465,203 | B2 * | 6/2013 | Barker | A61B 6/4405 378/197 |

(Continued)

*Primary Examiner* — David J Makiya
*Assistant Examiner* — Soorena Kefayati

(57) ABSTRACT

A mobile x-ray apparatus having wheels for manual transport and an x-ray tube support attached to a base. The apparatus may be rolled by pushing and/or pulling the base, the support, or the x-ray tube. A brake is associated with at least one of the wheels to prevent rolling the apparatus when manually positioning the x-ray tube. The brake may be engaged from an actuator on the tube head, on the support, or on the base.

17 Claims, 6 Drawing Sheets

(56) References Cited

U.S. PATENT DOCUMENTS

| | | | | |
|---|---|---|---|---|
| 8,480,303 B2* | 7/2013 | Hartwich | A61B 6/4441 | 378/193 |
| 8,553,842 B2* | 10/2013 | Moon | A61B 6/4452 | 378/115 |
| 8,568,028 B2* | 10/2013 | Wendlandt | A61B 6/447 | 378/193 |
| 8,636,410 B2* | 1/2014 | Yao | A61B 6/4405 | 378/197 |
| 8,840,304 B2* | 9/2014 | Perez Zarate | A61B 6/4405 | 378/197 |
| 8,876,379 B2 | 11/2014 | Dirisio et al. | | |
| 9,351,890 B2* | 5/2016 | Hough | A61G 5/14 | |
| 9,475,472 B2* | 10/2016 | Sakashita | B60T 7/042 | |
| 9,693,746 B2* | 7/2017 | Ancar | A61B 6/08 | |
| 2010/0322377 A1* | 12/2010 | Niizeki | A61B 6/04 | 378/20 |
| 2011/0058656 A1 | 3/2011 | Hartwich et al. | | |
| 2011/0162141 A1* | 7/2011 | Lemire | A61G 7/005 | 5/510 |
| 2012/0195405 A1* | 8/2012 | Woudstra | A61N 5/10 | 378/65 |
| 2012/0219122 A1 | 8/2012 | Herrmann et al. | | |
| 2013/0039473 A1* | 2/2013 | Kojima | A61B 6/4405 | 378/91 |
| 2013/0077765 A1* | 3/2013 | Welsh | A61B 6/105 | 378/198 |
| 2013/0121477 A1* | 5/2013 | Lee | H05G 1/02 | 378/198 |
| 2013/0272499 A1* | 10/2013 | Simmons | G01N 23/04 | 378/62 |
| 2014/0093040 A1* | 4/2014 | Omura | A61B 6/4405 | 378/62 |
| 2014/0093051 A1* | 4/2014 | Nishimura | A61B 6/4405 | 378/198 |
| 2014/0105358 A1* | 4/2014 | Nishimura | A61B 6/4233 | 378/62 |
| 2015/0201899 A1* | 7/2015 | Uchinomiya | A61B 6/4405 | 378/62 |
| 2015/0374314 A1* | 12/2015 | Maack | A61B 6/06 | 378/62 |
| 2016/0038109 A1* | 2/2016 | Fortuna | A61B 6/4447 | 378/64 |
| 2016/0058402 A1* | 3/2016 | Okuno | A61B 6/4405 | 378/193 |
| 2017/0020479 A1* | 1/2017 | Shimohira | A61B 6/4405 | |

* cited by examiner

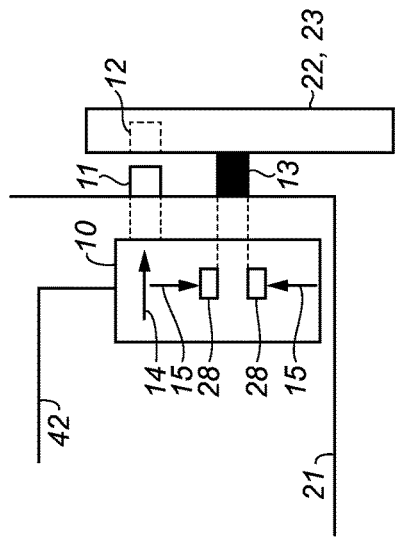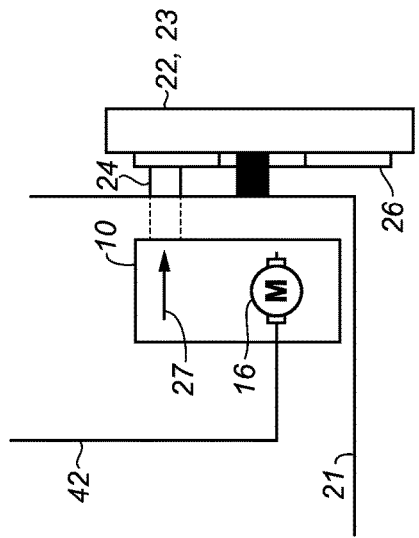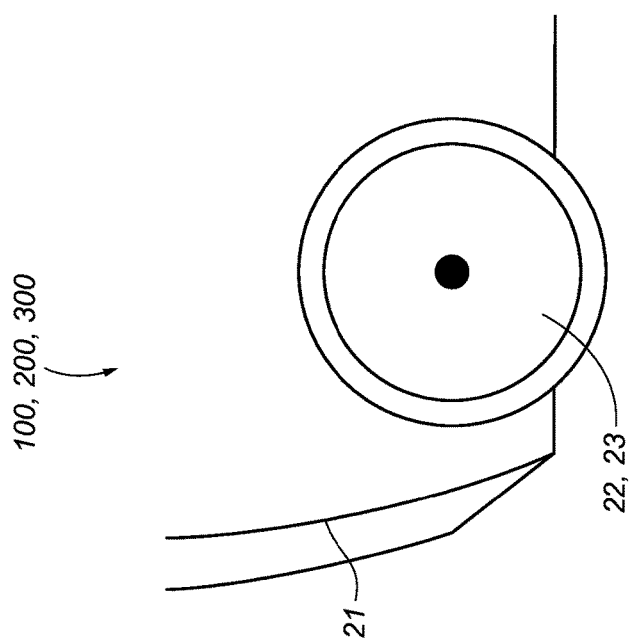

DIGITAL X-RAY IMAGING APPARATUS AND METHOD

CROSS REFERENCE TO RELATED APPLICATIONS

This application claims priority to U.S. Patent Application Ser. No. 62/036,287, filed Aug. 12, 2014, in the name of Wendlandt et al., and entitled DIGITAL X-RAY IMAGING APPARATUS AND METHOD, which is hereby incorporated by reference herein in its entirety.

This application is related in certain respects to: U.S. Pat. No. 8,568,028, filed Oct. 18, 2010 and issued Oct. 29, 2013, in the name of Wendlandt, et al., and entitled MOBILE RADIOGRAPHY UNIT HAVING COLLAPSIBLE SUPPORT COLUMN; U.S. Pat. No. 8,876,379, filed Apr. 11, 2011 and issued Nov. 4, 2014, in the name of DiRisio, et al., and entitled COLLAPSIBLE COLUMN MOVEMENT APPARATUS FOR MOBILE X-RAY DEVICE; and U.S. Pat. No. 6,409,382, filed Mar. 28, 2001 and issued Jun. 25, 2002, in the name of Akutsu, et al., and entitled MOBILE X-RAY APPARATUS, all of which are hereby incorporated by reference herein in their entirety.

BACKGROUND OF THE INVENTION

The subject matter disclosed herein relates to a mobile x-ray apparatus, in particular, to a mobile x-ray apparatus without a motorized mechanical assist that is transportable entirely by manually rolling the apparatus.

Mobile x-ray apparatuses are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

Apparatus and methods of the present disclosure address the need for a mobile radiography unit that can be readily wheeled from one place to another within a treatment facility. An object of the present disclosure is to provide a mobile x-ray apparatus which makes it possible to adjust the position of the x-ray tube head rapidly when moving the apparatus into a position for capturing an x-ray image of a patient. Some mobile x-ray apparatuses, such as U.S. Pat. No. 6,409,382 to Akutsu, et. al., referenced above, include a drive motor for driving the plurality of wheels due to the difficulty of manually manipulating the apparatus.

The discussion above is merely provided for general background information and is not intended to be used as an aid in determining the scope of the claimed subject matter.

BRIEF DESCRIPTION OF THE INVENTION

A mobile x-ray apparatus includes wheels, for manual transport, and an x-ray tube support attached to a base. The apparatus may be rolled by pushing and pulling the base, the support, or the x-ray tube head. A brake is associated with at least one of the wheels to prevent rolling the apparatus when manually positioning the tube head. The brake may be engaged using an actuator located on the tube head, the support, or on the base. An advantage that may be realized in the practice of some disclosed embodiments of the mobile x-ray apparatus is easier manual positioning of the tube head. The present patent application is directed to a mobile x-ray apparatus having non-driven wheels. That is, a mobile x-ray apparatus which does not include a motor or other mechanical assistance for driving the wheels.

In one embodiment, a mobile x-ray apparatus has wheels and a support assembly attached to a base, and an x-ray tube head attached to the support assembly. The support assembly and the tube head are configured to enable rolling the apparatus by disengaging a brake using an actuator on the tube head, or on the support assembly, while pushing or pulling the tube head. An operator may engage and disengage the brake by using an actuator when positioning the tube head over a patient.

In another embodiment, a method for capturing an x-ray image using a manually movable x-ray apparatus is disclosed. The mobile x-ray apparatus may be rolled to a base position, relative to a patient, and then a brake is engaged to prevent further rolling of the apparatus. The x-ray tube head may then be manually positioned while releasing the brake, if desired, to allow the apparatus to roll. An actuator for engaging and disengaging the brake is conveniently placed on or proximate the tube head.

In another embodiment, a method for capturing an x-ray image using a mobile x-ray apparatus is disclosed. The apparatus is positioned by rolling a mobile base of the apparatus into position near a bed side, for example, then adjusting the x-ray tube head to a first imaging position. An actuator mounted near the x-ray tube head releases a brake on at least one of the wheels to enable easier positioning of the x-ray tube head by rolling the mobile base.

In another embodiment, a mobile x-ray apparatus includes an x-ray tube mounted on an arm whereby the arm is mounted on a mobile base having non-driven wheels. A brake is associated with at least one of the wheels and is controlled by an actuator mounted on the apparatus near the x-ray tube.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 4A-C are schematic diagrams of exemplary wheel and brake assemblies;

DETAILED DESCRIPTION OF THE INVENTION

Figure 1:
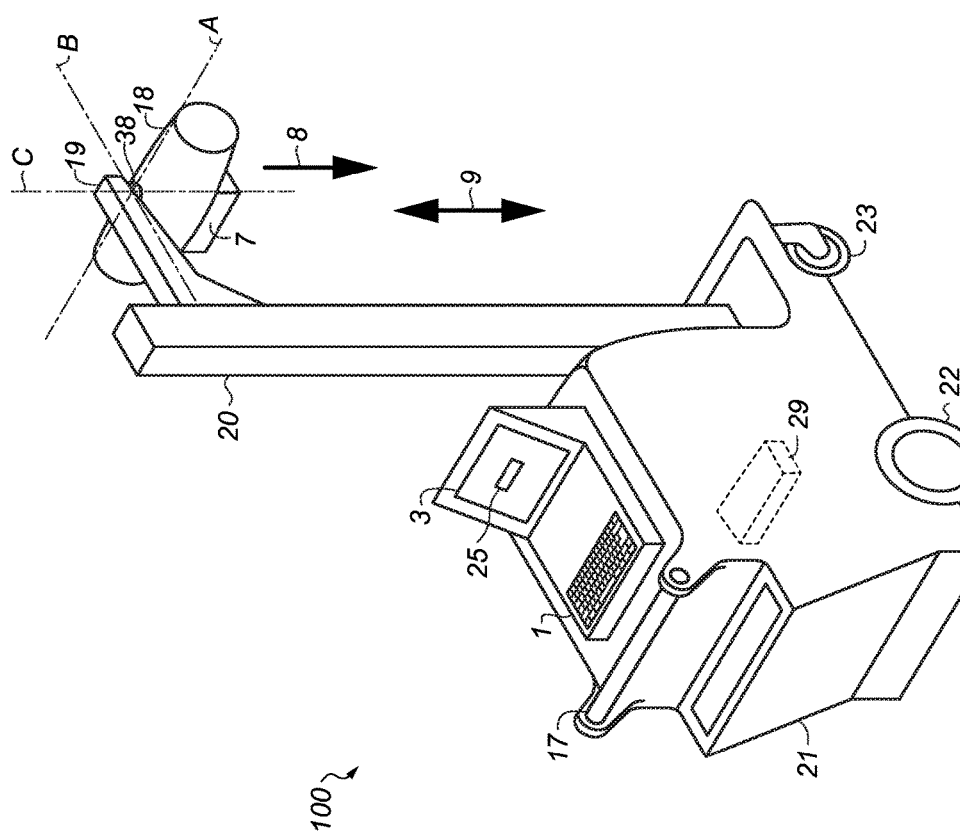
FIG. 1 is a perspective view of an exemplary mobile x-ray apparatus.

Referring to FIG. 1, a mobile x-ray apparatus 100 includes an x-ray source assembled in an x-ray tube, which assembly may also be referred to as a tube head 18. The mobile x-ray apparatus 100 further includes a vertically moveable arm 19 supporting the x-ray tube head 18, a collimator 7, a base 21, a column 20 having one end mounted on the base 21, whereby the arm 19 may move up and down along the column 20 in vertical directions indicated by the arrow 9. Thus, the arm 19 is attached to the column 20 by a height adjustable joint. The column 20 together with the arm 19 may be referred to as a support assembly having one end attached to the base 21 and having another opposite end attached to the tube head 18, using a rotatable joint 38. The base 21 has a plurality of non-driven wheels, 22, 23, wherein a pair of pivotable wheels 23 may be referred to herein as front wheels (including a right wheel and a left wheel) and a pair of non-driven unpivotable wheels 22 which may be referred to herein as rear wheels (including a right wheel and a left wheel). An operational handle bar 17 is attached to the base 21. The handle bar 17 may include switches or other actuators attached thereto so that they may be activated while an operator grasps the handle bar 17. An operator may manually move the mobile x-ray apparatus 100 by pushing and/or pulling the handle bar 17 to roll the mobile x-ray apparatus into a position, as desired, using the wheels 22, 23.

Figure 2:
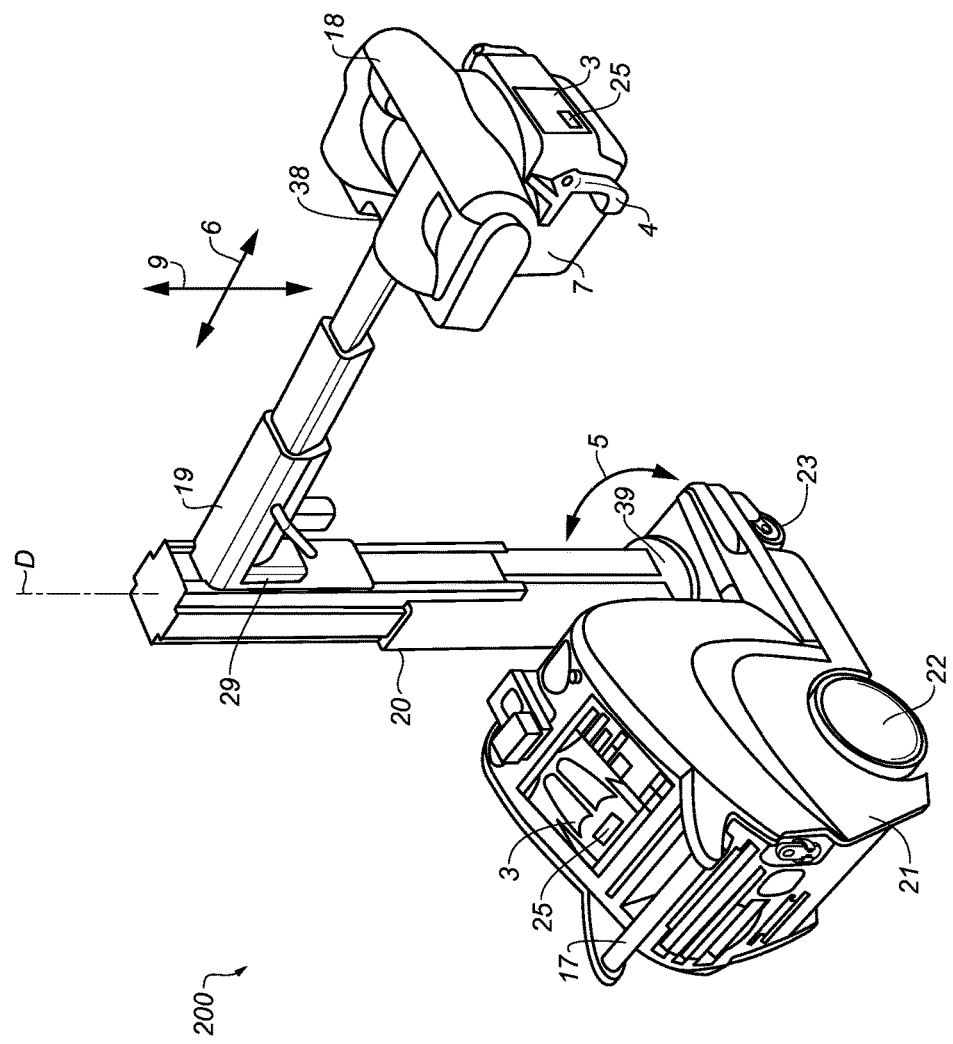
FIG. 2 is a perspective view of another exemplary mobile x-ray apparatus.
Figure 5:
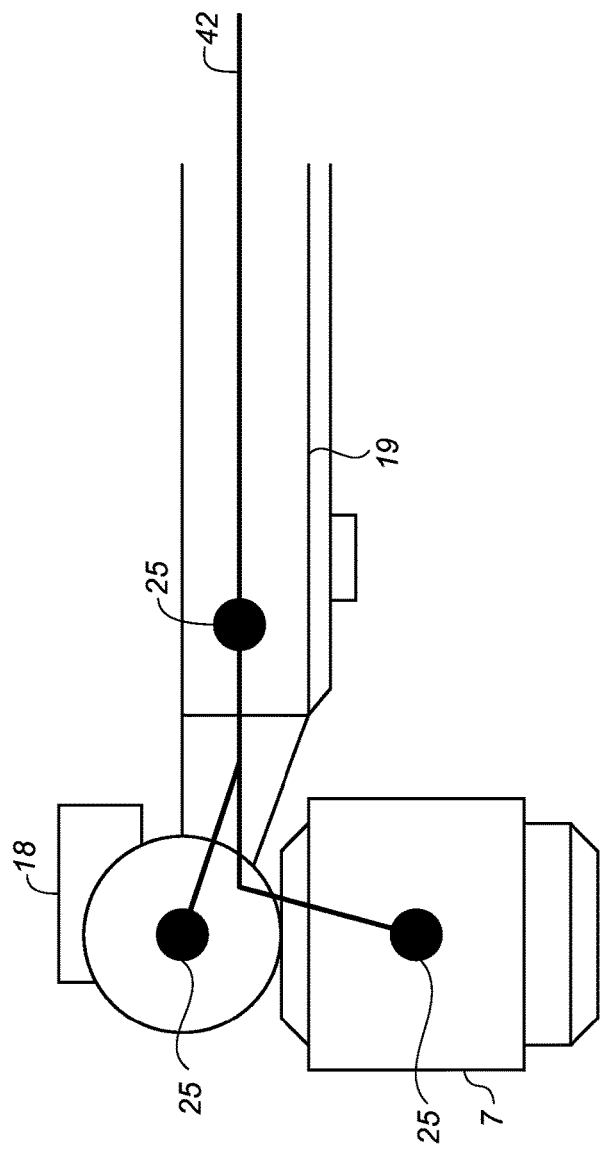
FIG. 5 is a schematic diagram of exemplary actuator locations.

An operator may input commands and requests for operating the x-ray apparatus 100 using an input device 1, such as a keyboard or mouse, and may also use a touch sensitive display screen 3 for inputting commands and requests. The mobile x-ray apparatus 100 may include a programmed processing system 29 housed in the base 21 and communicatively connected to the input device 1 and the touch sensitive display screen 3, and to at least one actuator 25 (FIG. 5). The processing system 29 enables the operator to enter commands and requests via the input device 1, the touch sensitive display screen 3, or via actuators 25, which commands and requests may be processed by the processing system 29 and cause control signals to be transmitted to other components of the mobile x-ray apparatus 100, as described herein. It should be noted that a touch sensitive display screen 3 may be duplicated and positioned at the tube head 18, as illustrated in FIG. 2, in addition to the touch sensitive display screen 3 positioned on the base 21, as illustrated in FIG. 1. The mobile x-ray apparatus 100 is light enough so that a motor or other powered driving mechanism is not required to transport the mobile x-ray apparatus 100. One or more of the wheels 22, 23 may include an associated brake, as described herein.

The arm 19 may be configured to support the x-ray tube head 18 and allow the tube head 18 to be rotated about orthogonal axes A, B and C, using a rotatable joint 38 to attach the tube head 18 to the arm 19. The arm 19 may include a telescoping structure (FIG. 2) so that the arm 19 and tube head 18 may be extended away from or toward column 20. Thus, the x-ray irradiation aperture of the x-ray tube head 18 may be aimed in all directions by manually rolling the apparatus 100 using wheels 22, 23, and manipulating the tube head 18 about orthogonal axes A, B and C, as desired. The exemplary mobile x-ray apparatus 100 is structured to maintain balance without tipping when the arm 19 moves up and down along the column 20 and when the arm 19 is maximally extended away from column 20. As shown in exemplary FIG. 1, an x-ray irradiation aperture of the x-ray tube head 18 is aimed downward in the direction indicated by arrow 8.

Alternative mobile x-ray apparatus configurations may be suitable for the invention as claimed herein. For example, FIG. 2 illustrates an alternative mobile x-ray apparatus 200, which also includes the components described in the mobile x-ray apparatus 100 shown in FIG. 1, unless specifically described herein as excluding such components. Like parts of FIG. 2 are numbered the same as in FIG. 1 and are similarly operable unless otherwise described herein. Mobile x-ray apparatus 200 includes a column 20 that is rotatably attached at one end to base 21, using a rotatable joint 39. Thus, the column 20 may be rotated about axis D in the directions indicated by arrow 5. Telescoping arm 19 may be used to move the tube head 18 closer to or further from the column 20, as indicated by the arrow 6, by manually collapsing or extending (pushing or pulling) the tube head 18. The tube head 18 may or may not be provided with handles 4 for easier manipulation. The tube head 18 may be rotated about three axes as described with reference to the mobile x-ray apparatus 100 of FIG. 1, using rotatable joint 38. The mobile x-ray apparatus 200 further includes a vertically moveable arm 19 whereby the arm 19 may move up and down along the column 20 in directions indicated by the arrow 9. Thus, the arm 19 is attached to the column 20 by a height adjustable joint 29. The column 20 together with the arm 19 may be referred to as a support assembly which is attached at one end to the base 21, using a rotatable joint 39, and at a second end to the tube head 18, also using a rotatable joint 38. It will be apparent to one skilled in the art that the column 20 may include a rotatable joint 39 at various locations on the column 20, such as near the top of the column, other than at its first end which is attached to the base 21. While the arm 19 can be comprised of a single component, as illustrated in FIG. 1, or multiple components such as the collapsible arm 19 illustrated in FIG. 2, other configurations for the support assembly are possible and are considered to be within the scope of the presently claimed invention.

In one embodiment, the weight of the mobile x-ray apparatus 200 allows it to be moved manually without power or other mechanical or electromechanical assistance. As such, the base 21 generally has rear wheels 22, which are not pivotable, and front wheels 23 which are pivotable, for example like casters, as described with reference to FIG. 1. Rubber tires may be used for the wheels 22, 23, and the base 21 is designed such that it can freely move, for example, by being rolled into and out of a patient's room, an operation room, or an elevator. While the wheels 22, 23 may each include components such as a rigid rim supporting an annular rubber strip, tire, or other non-slip material, and bearings for reducing rotational friction, the wheels 22, 23, may also include a one piece construction mounted on a support such as an axle. The braking system for the wheels 22, 23, is described herein.

Alternative mobile x-ray apparatus configurations may be suitable for the invention as claimed herein. For example, FIG. 3A illustrates an alternative mobile x-ray apparatus 300, which also includes the components described in the mobile x-ray apparatus 100 shown in FIG. 1, unless specifically described herein as excluding such components. Like parts of FIG. 3A are numbered the same as in FIG. 1 and are similarly operable unless otherwise described herein. Mobile x-ray apparatus 300 includes a base 21 having a plurality of non-driven wheels, 22, 23, wherein one or more pivotable wheels 23 may be attached to a front portion of the base 21, and a pair of non-driven wheels 22 may be attached to a portion of the base 21 rearward of the front portion. Mobile x-ray apparatus 300 includes a jointed arm composed of two arm portions 19a and 19b. Arm portion 19a may be rotatably attached to base 21 of mobile x-ray apparatus 300 via a rotatable joint 30 that is rotatable about axis E in the directions indicated by arrow 32, as well as being rotatable about axis F. Arm portion 19a is attached to arm portion 19b by a rotatable elbow joint 34 that allows arm portions 19a and 19b to rotate, relative to each other, about axis G in the directions indicated by arrow 33. The tube head 18 may be grasped and manipulated by an operator so that arm portion 19a may be rotated about either or both of the axes E, F, as well as arm portion 19b being rotated about axis G. The tube head 18 may be rotated about three axes as described with reference to mobile x-ray apparatus 100 of FIG. 1, using rotatable joint 38. The arm portions 19a, 19b, and the rotatable joint 34, may be referred to as a support assembly having one end attached to the base 21, using a rotatable joint 30, and having another opposite end attached to the tube head 18, also using a rotatable joint 38. The support assembly including arm 19, arm portions 19a, 19b, and/or column 20, has been described herein as having multiple alternative configurations, such as having a single component, as illustrated in FIG. 1, a collapsible configuration as illustrated in FIG. 2, and a hinged, or jointed configuration as illustrated in FIG. 3. It will be apparent to one skilled in the art that the support assemblies described herein may be modified in various suitable combinations, all of which are contemplated as part of the invention claimed herein.

Figure 3B:
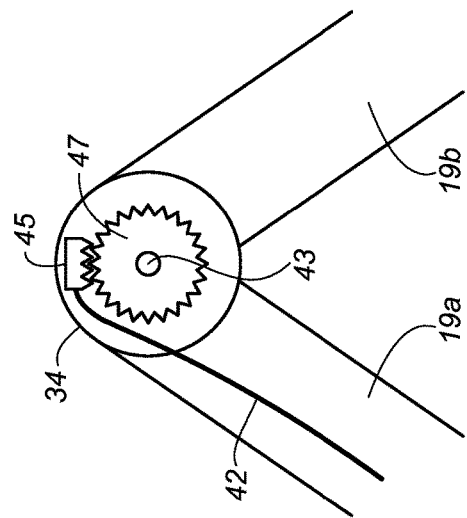
FIG. 3B is a schematic diagram of an exemplary joint and locking mechanism.
Figure 3A:
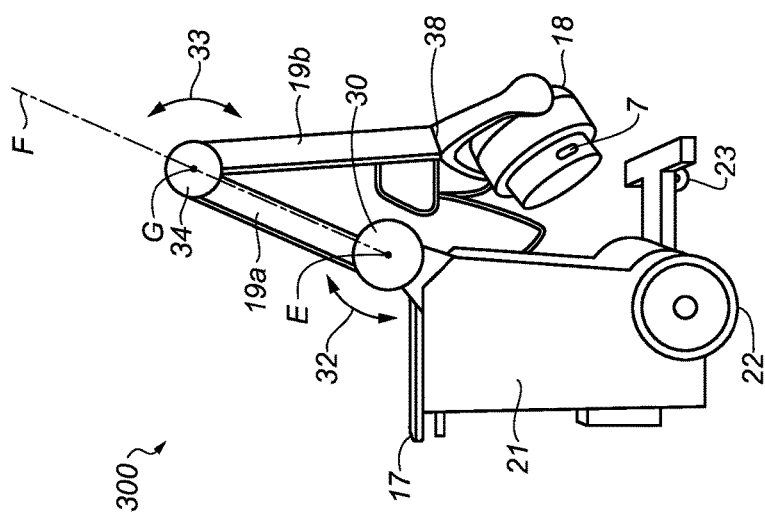
FIG. 3A is a perspective view of another exemplary mobile x-ray apparatus.

FIG. 3B illustrates an exemplary rotatable elbow joint 34 whereby arm portions 19a, 19b, are connected via elbow joint 34 and are rotatable with respect to each other about a shaft 43 disposed at axis G. A rotating plate 47 may be rigidly attached at elbow joint 34 to one of the arm portions 19a, 19b. The rotating plate 47 may include teeth at a portion of the rotating plate 47 facing locking mechanism 45. The locking mechanism 45 may be attached to one of the arm portions 19a, 19b, and be configured with immovable teeth that mate with the rotating plate 47 to lock the rotating plate 47 when the locking mechanism 45 is activated, thereby preventing rotation of the arm portions 19a, 19b, about elbow joint 34. An actuator line 42 may be connected to the locking mechanism 45 to activate and deactivate the locking mechanism 45. The actuator line 42 may include an electrical, mechanical, or electromechanical activation assembly. In one embodiment, the actuator line 42 may include a flexible cable enclosed in a flexible cable housing, described herein, that is connected at one end to the locking mechanism 45 that causes the locking mechanism 45 to engage and mate with the rotating plate 47 to prevent its rotation and, hence, the rotation of the elbow joint 34. In one embodiment, the actuator line 42 may include a conductive electrical signal line that may activate and deactivate the locking mechanism 45 to engage with and disengage from the rotating plate 47.

In one embodiment, the actuator line 42 may include a conductive wire, connected to a solenoid in the locking mechanism 45, which transmits an electric signal to the solenoid that causes the locking mechanism 45 to engage the rotating plate 47 to prevent its movement and, hence, the rotation of the elbow joint 34. Another electric signal transmitted over actuator line 42 may cause the locking mechanism 45 to disengage. In this embodiment, the conductive wire of the actuator line 42 may be electrically coupled to one or more actuators 25 that may be activated, as desired, by an operator to engage the locking mechanism 45. Although the locking mechanism 45 has been described herein as implemented in the elbow joint 34, similar locking mechanisms may be employed in the height adjustable joint 29 (FIG. 2) to prevent vertical movement thereof; in the three axes rotatable joint 38 (FIGS. 1, 2 and 3A) to prevent rotation thereof; in the rotatable joint 39 (FIG. 2) at the base 21 end of the support assembly to prevent rotation thereof; and in the rotatable joint 30 (FIG. 3A) at the base 21 end of the support assembly to prevent rotation thereof.

In operation, since the mobile x-ray apparatus 100, 200, 300 does not include a drive motor for driving the wheels, the mobile x-ray apparatus 100, 200, 300 may be moved or rolled using manual manipulation, e.g., pushing and pulling, by an operator or other technician. When not being moved by the operator, the apparatus can be held in a stationary position by one or more brakes associated with one or more of the wheels. With reference to FIG. 4A, a side view of one exemplary wheel 22, 23, attached to a base 21 of the mobile x-ray system 100, 200, 300, is illustrated. FIGS. 4B-4C illustrate a front transparent schematic view of the exemplary wheel 22, 23, and a brake mechanism 10 that is configured to lock the wheels 22, 23, in response to an operator activation of an actuator 25. The particular brake mechanisms described and illustrated in FIGS. 4B-4C may be interchangeable, may be used solely, or used in various combinations. The FIGS. 4B-4C are not intended to illustrate required combinations of brake assemblies and are only illustrative, descriptive, and enabling examples. Similar to the locking mechanism 45 described herein, the brake mechanism 10 may be connected to, and controllable by, one or more actuators via an actuator line 42. The descriptions herein of the actuator line 42 used with the brake mechanism 10 is applicable to the actuator line 42 used with the locking mechanism 45, and vice versa. The actuator lines 42 connected to the locking mechanism 45, or connected to one or more other locking mechanisms for preventing rotation of the rotatable joints as described herein, and the brake mechanism 10, may be commonly controlled by each of one or more actuators 25 described herein. The actuator line 42 may include a mechanical, electrical or electromechanical actuator line, as mentioned herein. In one embodiment, the actuator line 42 may include an elongate flexible cable enclosed by a flexible cable housing. Such a cable may be incompressible in a lengthwise direction but flexible transverse to its lengthwise direction. The cable may be set by an operator, for example, by pulling an actuator comprising a cable handle attached to an operator end of the cable, or by pushing an actuator comprising a button or plunger attached to the operator end of the cable, to set the cable in a brake engagement position, which handle, button, or plunger, may then be released at any time by the operator, as desired, to disengage the brake.

In one embodiment, the actuator line 42 may include a conductive wire which transmits an electric signal to the brake mechanism 10 that causes the brake mechanism 10 to be engaged and prevent rotation of the wheels 22, 23. The conductive wire of the actuator line 42 may be electrically coupled to one or more actuators 25 (FIGS. 1, 2, 5) that may be activated, as desired, by an operator to engage the brake mechanism 10.

Referring to FIGS. 4B-4C, in one embodiment, a cable of actuator line 42 may be attached at the brake mechanism 10 to a bolt 11, for example, by using a mechanical force 14 causing the bolt 11 to travel into a rim slot 12 within a rim of the wheel 22, 23, to prevent rotation thereof. In one embodiment, the cable of actuator line 42 may be attached at the brake mechanism 10 to a clamp, or drum, device 28, for example, by causing the clamp 28 to exert a frictional force 15 against an axle 13 attached to the wheel 22, 23, to prevent rotation thereof. In one embodiment, a cable in the actuator line 42 may be attached at the brake mechanism 10 to a clamp, or drum, device 24, for example, by causing the clamp 24 to exert a frictional force 27 against a pad, or disc, 26 attached to the wheel 22, 23, to prevent rotation thereof. Other embodiments of the brake mechanism 10 may include a magnetic brake or other suitable brake mechanisms presently known or later developed, which are considered to be within the scope of the presently claimed invention. The actuator line 42 may be coupled at its opposite end to one or more actuators 25 that may be activated, as desired, by an operator to engage the brake mechanism 10. Such an actuator may include a handle, a button, switch, plunger, or other means that causes the cable to activate brake mechanism 10.

In one embodiment, the actuator line 42 may transmit an electric signal that activates an electric motor 16 in the brake mechanism 10 (FIG. 4C), which motor 16 then provides the mechanical force 14 for the bolt 11, the mechanical force 15 for the clamp 28, or the mechanical force 27 for the clamp 24. In one embodiment, the brake mechanism 10 may include a solenoid to provide the mechanical forces. The electric signal may be used to toggle the brake mechanism 10 between an activated state and a deactivated state to engage and disengage the brake, respectively, as desired. Electric signals transmitted over one or more actuator lines 42 to disengage brake mechanisms 10 may also be commonly transmitted to one or more locking mechanisms 45 to prevent rotation of the rotatable joints connected thereto. Similarly, electric signals transmitted over actuator lines 42 to engage one or more brake assemblies 10 may also simultaneously cause locking mechanisms 45 at one or more rotatable joints to disengage. Signals transmitted over actuator line 42 to disengage and engage the brake mechanism 10 may be the same signals to engage and disengage, respectively, any one or more locking mechanisms used at one or more of the joints described herein. Such signals may be transmitted as separate signals which require a controller to receive and interpret the signals at each corresponding locking mechanism 45 or brake mechanism 10. As described previously, locking mechanisms as described herein may be connected to: the height adjustable joint 29 (FIG. 2) to prevent/allow vertical movement thereof; the three axes rotatable joint 38 (FIGS. 1, 2 and 3A) to prevent/allow rotation thereof; the rotatable joint 39 (FIG. 2) at the first end of the support assembly to prevent/allow rotation thereof; and the rotatable joint 30 (FIG. 3A) at the first end of the support assembly to prevent/allow rotation thereof.

As illustrated in FIG. 5, one or more actuators 25, accessible to an operator or technician, may be located at any portion of the mobile x-ray apparatus 100, 200, 300, such as at the tube head 18, the collimator 7, or on the arm 19. Other locations for placing an actuator 25 may include the base 21 or on the handle bar 17. As described herein, the actuators 25 may be controlled by the processing system 29 to manage transmission of signals over actuator lines 42. For example, if separate signals are used to activate and deactivate locking mechanisms 45 or brake mechanisms 10, the processing system 29 may generate the separate signals to be transmitted over the actuator lines 42. Thus, the actuator lines 42 may be electrically connected to one or more actuators 25, the processing system 29, one or more locking mechanisms 45, and one or more brake mechanisms 10.

As described herein, the actuators 25 may include buttons, switches, or other devices that may be activated by an operator to generate electric signals transmitted over actuator lines 42. In one embodiment, actuators 25 may each generate the same signal each time they are activated by an operator, whereby each successive signal may alternate between causing engagement and disengagement of one or more brake mechanisms 10 and simultaneous deactivation and activation of one or more locking mechanisms 45, respectively, in what may be referred to as a toggle mode of operation. In one embodiment, actuators 25 may each include two buttons, or switches, whereby one button is dedicated for engaging a brake mechanism 10 or activating locking mechanism 45, and a second button is dedicated for disengaging the brake mechanism 10, and deactivating the locking mechanism 45. In one embodiment, the actuators 25 may each include a timer that is automatically started by an operator activating an actuator 25. The timer may be preset for a selected time duration after which, when the timer times out or expires, the activation or deactivation that was initiated by an operator is automatically terminated. In one embodiment, the actuators 25 may be biased to a first position which may be selected as an activated or deactivated position. Such a bias may include a spring bias mechanism, for example. In this embodiment, operator activation of the actuator 25 may require the operator to maintain the actuator in a second position. For example, an actuator 25 may comprise a spring-biased button requiring the operator to hold down the button continuously in order to disengage (or engage) the brake mechanism 10. The operator may then release, or let go of, the spring-biased button, when desired, to automatically reengage (or disengage) the brake mechanism 10. In one embodiment, a touch sensitive display screen 3, either on the base 21 or on the tube head 18, may include one or more regions that act as a touch sensitive actuator 25. These touch sensitive actuator regions may be operable in a similar fashion as the actuators 25 described above. In one embodiment, it may be desirable that one or more locking mechanisms 45 be activated whenever the brake mechanism 10 is disengaged in order to assist an operator to roll the mobile x-ray apparatus 100, 200, 300, using the wheels 22, 23. Such an embodiment helps to prevent rotation of one or more of the rotatable joints when an operator desires to roll the mobile x-ray apparatus 100, 200, 300, by pushing or pulling on the tube head 18, or pushing or pulling the arm 19. Thus, the signals transmitted over actuator lines 42 may be controlled to automatically activate the one or more locking mechanisms 45 whenever a brake mechanism 10 is disengaged.

As described herein, the actuators 25 may include mechanical actuators 25 that do not transmit electric signals. Such actuators 25 may be connected to one or more brake mechanisms 10 or locking mechanisms 45 by a cable, as described herein, which clamps one or more wheels 22, 23, or blocks rotational movement of the wheels 22, 23, or of the rotating plate 47, as described herein. The actuators 25 and actuator lines 42 may include both a mechanical cable assembly and electrical signal lines. In one embodiment, an electrical signal line embodiment of the actuator line 42 may be connected to and controllable by the processing system 29 in the base 21 to control transmission of electric signals over the actuator line 42 in response to operator action. As described herein, an operator may use an actuator 25 comprising a touch screen control on display 3 to activate the brake mechanism 10 or the locking mechanism 45, or the operator may provide an input to the processing system 29 using the keyboard 1. The touch screen control on display 3 may be located on the base 21, as shown in FIGS. 1 and 2, or the touch screen control on display 3 may be located at the tube head 18, as shown in FIG. 2, or both, as shown in FIG. 2.

Figure 6:
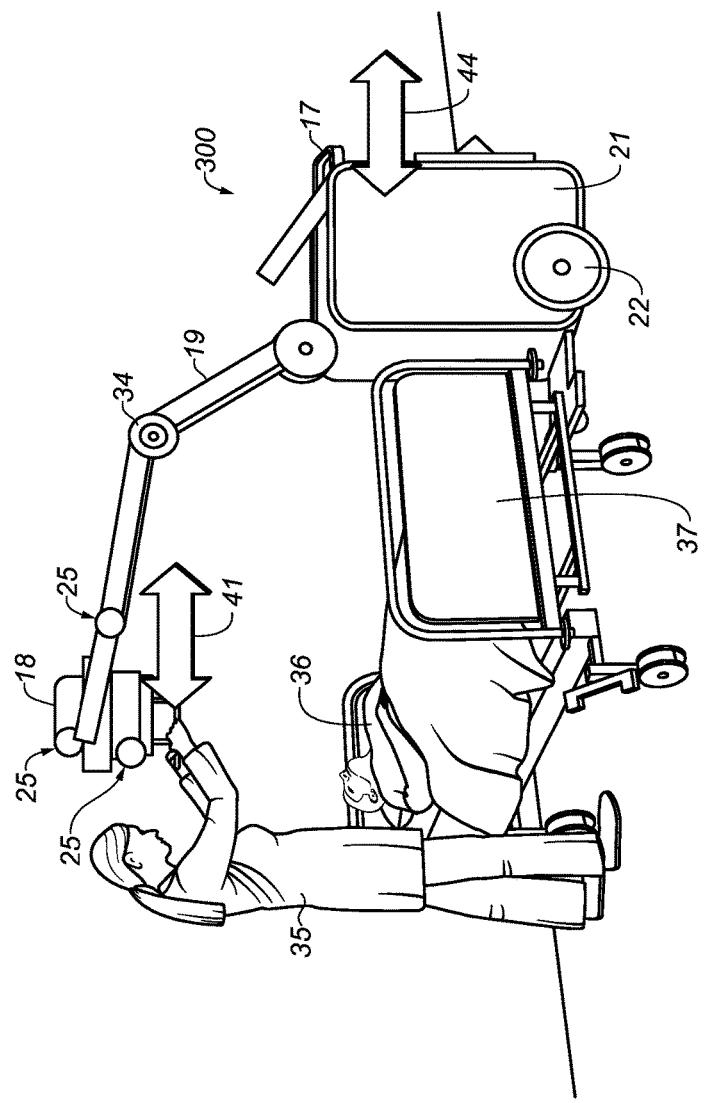
FIG. 6 is a perspective view showing an exemplary method of operating the mobile x-ray apparatus.

With reference to FIG. 6, there is illustrated an exemplary method of operation of an exemplary mobile x-ray apparatus 300, which mobile x-ray apparatus 300 may include other embodiments, as described herein. In one embodiment, to operate the mobile x-ray apparatus 300 an operator 35 may push or pull the mobile x-ray apparatus 300 using handle bar 17 to move the mobile x-ray apparatus 300 to one side of a bed 37, using wheels 22, 23 (front wheel or wheels 23 not visible), as shown in FIG. 6. The operator 35 may stop or lock the mobile x-ray apparatus 300 in a stationary base position by actuating a wheel brake mechanism 10, as described herein. The operator 35 may then walk to a side of the bed 37 opposite the mobile x-ray apparatus 300 to prepare to position the x-ray tube head 18 relative to the patient 36. The operator 35 may adjust a position of the tube head 18 vertically, horizontally, and rotationally, by pulling, pushing, or otherwise manipulating the tube head 18, as desired, so as to properly aim an x-ray radiation aperture of the tube head 18 at a target portion of the patient 36. In some circumstances, it may be preferable to move the entire mobile x-ray apparatus 300 to better aim the x-ray radiation aperture at a desired target region of the patient 36. By locating actuators 25 on or near the tube head 18, as illustrated in FIGS. 2 and 5, they remain within easy reach of the operator 35 and may be activated by the operator 35 to disengage the wheel brake mechanism 10 and allow movement of the entire mobile x-ray apparatus 300 by pushing or pulling the tube head 18. Thus, the operator 35 need not walk around the bed 37 back to the base 21 at the opposite side of the bed to activate actuators 25 located at the base 21. The operator 35 may, for example, push or pull the tube head 18 in the directions indicated by arrow 41 in order to move the entire mobile x-ray apparatus 300, including base 21, in the directions indicated by the arrow 44. With the brake mechanism 10 released, the operator may push/pull the tube head 18 or arm 19, which, in turn, easily moves the base 21 to a new position. As described herein, the disengagement of one or more brake mechanisms 10 may automatically activate one or more locking mechanisms 45 in the elbow joint 34, and in other ones of the rotatable joints, as necessary, to allow easier movement of the entire mobile x-ray apparatus 300 under operator 35 control. This allows the operator 35 to adjust the position of tube head 18 without having to walk back around to the other side of the bed 37 in order to make fine adjustments to the position of the mobile x-ray apparatus 300.

As will be appreciated by one skilled in the art, aspects of the present invention may be embodied as a system or method operable under computer program control. Accordingly, aspects of the present invention may take the form of an entirely hardware embodiment, an entirely software embodiment (including firmware, resident software, microcode, etc.), or an embodiment combining software and hardware aspects that may all generally be referred to herein as a processing system.

Program code and/or executable instructions embodied on a computer readable medium may be transmitted using any appropriate medium, including but not limited to wireless, wireline, optical fiber cable, RF, etc., or any suitable combination of the foregoing, and may be stored in a memory accessible to the processing system. Any combination of one or more processing systems may be utilized. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with a processing system.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:
1. A mobile x-ray apparatus, comprising:
a base having attached thereto a plurality of non-driven wheels, the base configured to enable manual rolling of the apparatus along a floor by pushing and pulling the base;
an x-ray tube support assembly attached to the base, the support assembly having a non-extended position when the apparatus is not being used for x-ray imaging and an extended position when the apparatus is used for x-ray imaging, the support assembly configured to enable said manual rolling of the apparatus along the floor by pushing and pulling the support assembly in the extended position;

an x-ray tube head mounted on the x-ray tube support assembly, the tube head configured to enable said manual rolling of the apparatus along the floor by pushing and pulling the tube head while the support assembly is in the extended position;

a brake associated with at least one of the non-driven wheels, the brake configured to prevent said manual rolling of the apparatus while the support assembly is in the extended position when the brake is engaged with at least one of the non-driven wheels; and at least one actuator mounted on the apparatus, the at least one actuator configured to engage and disengage the brake, wherein the at least one actuator is mounted only on the tube head, only on the support assembly, or on both the tube head and the support assembly.

2. The apparatus of claim 1, wherein the support assembly comprises a first end attached to the base, a second end attached to the tube head, a rotatable joint between the first end and the second end, and a locking mechanism that is automatically activated to prevent rotation of the rotatable joint when the at least one actuator is activated to disengage the brake.

3. The apparatus of claim 1, wherein the actuator is configured to deactivate the brake while the actuator is held in a first position by an operator, and wherein the actuator is configured to activate the brake when the actuator is released by the operator.

4. The apparatus of claim 1, wherein the at least one actuator is configured to toggle between engaging the brake and disengaging the brake with each activation of the at least one actuator by the operator.

5. The apparatus of claim 1, wherein the actuator is configured to disengage the brake for a finite time in response both to an operator activating the at least one actuator and to a timer connected to the actuator, whereby an expiration of the timer causes the at least one actuator to engage the brake.

6. A method for capturing an x-ray image using a manually movable mobile x-ray apparatus, the apparatus including a base having a plurality of non-driven wheels, an arm mounted to the base, and an x-ray tube head mounted on the arm, the method comprising:

manually rolling the mobile x-ray apparatus into a first base position relative to a patient using the plurality of non-driven wheels;

setting a brake associated with at least one of the plurality of non-driven wheels to prevent said at least one of the plurality of non-driven wheels from rolling;

moving the x-ray tube head away from the base to a first tube head position proximate to the patient by extending the arm; and manually pushing or pulling the tube head or the arm while the arm is extended, including manually activating an actuator mounted on the tube head or on the arm for releasing the brake to allow said at least one of the plurality of non-driven wheels to roll for manually rolling the apparatus to a second base position using the plurality of non-driven wheels.

7. The method of claim 6, wherein the step of manually rolling the apparatus includes manually pushing or pulling the base, the arm, the tube head, or a combination thereof.

8. The method of claim 6, wherein the step of moving the x-ray tube head away from the base includes rotating a joint at the x-ray tube head, rotating a joint in the base, rotating a joint in the arm between the base and the x-ray tube head, or a combination thereof.

9. The method of claim 6, wherein the step of releasing the brake includes manually holding the actuator in a first position by an operator while pushing or pulling the x-ray tube head and then releasing the actuator, toggling the actuator from an brake engage state to a brake-disengage state, releasing the brake for a time duration controlled by a timer whereafter the brake is reengaged, or a combination thereof.

10. A method for capturing an x-ray image of a patient using a mobile x-ray apparatus, the apparatus including a mobile base having a plurality of non-driven wheels, an arm mounted on the base, and an x-ray tube head mounted on the arm, comprising:

moving the mobile base to a first location relative to the patient by manually pushing or pulling the base thereby rolling the plurality of non-driven wheels;

engaging a brake to prevent rolling of at least one of the plurality of non-driven wheels;

extending the x-ray tube head away from the base to a first image capture position;

activating at least one actuator mounted on the tube head or arm to release the brake to allow rolling of said at least one of the plurality of non-driven wheels; and manually pushing or pulling the tube head to a second image capture position while the actuator is activated, wherein the manual pushing or pulling moves the mobile base to a second location relative to the patient by rolling the plurality of non-driven wheels.

11. The method of claim 10, wherein the step of manually pushing or pulling the tube head to a second image capture position comprises moving the tube head and the mobile base simultaneously.

12. The method of claim 10, further comprising reengaging the brake before activating the x-ray tube head to emit x-rays.

13. A mobile x-ray apparatus, comprising:

an x-ray tube head;

an arm, the arm movable to an extended position for activating the x-ray tube head and movable to a non-extended position for not activating the x-ray tube head, the x-ray tube head mounted on the arm;

a mobile base having only non-driven wheels for unassisted manual rolling of the apparatus over a floor, the arm mounted on the mobile base;

at least one brake associated with at least one of the wheels to prevent rolling of the at least one of the wheels; and at least one actuator mounted on the x-ray tube head or on the arm proximate the x-ray tube head for engaging and disengaging the at least one brake while the arm is in the extended position.

14. The apparatus of claim 13, wherein the actuator is configured to simultaneously disengage the at least one brake and to lock the movable arm to prevent movement of the arm.

15. The apparatus of claim 13, further comprising a display, the display comprises a region on the display that controls the actuator.

16. The apparatus of claim 13, further comprising a timer, wherein the timer is configured to begin timing upon an engagement or disengagement of the at least one brake, and wherein the timer is configured to terminate said engagement or disengagement of the at least one brake upon timing out.

17. The apparatus of claim 15, wherein the display is a touch screen display and the at least one actuator is activated to control the at least one brake by an operator touching the region on the display.

* * * * *